United States Patent
Dohrmann et al.

(10) Patent No.: US 11,923,058 B2
(45) Date of Patent: Mar. 5, 2024

(54) MOBILE SYSTEM FOR THE ASSESSMENT OF CONSUMER MEDICATION COMPLIANCE AND PROVISION OF MOBILE CAREGIVING

(71) Applicant: Electronic Caregiver, Inc., Las Cruces, NM (US)

(72) Inventors: Anthony Dohrmann, Las Cruces, NM (US); Bryan John Chasko, Las Cruces, NM (US); David W. Keeley, Frisco, TX (US)

(73) Assignee: Electronic Caregiver, Inc., Las Cruces, NM (US)

( * ) Notice: Subject to any disclaimer, the term of this patent is extended or adjusted under 35 U.S.C. 154(b) by 0 days.

(21) Appl. No.: 16/373,401

(22) Filed: Apr. 2, 2019

(65) Prior Publication Data

US 2019/0311792 A1  Oct. 10, 2019

Related U.S. Application Data

(60) Provisional application No. 62/655,582, filed on Apr. 10, 2018.

(51) Int. Cl.
*G16H 20/10* (2018.01)
*G06F 3/0484* (2022.01)
(Continued)

(52) U.S. Cl.
CPC ........... *G16H 20/10* (2018.01); *G06F 3/0484* (2013.01); *G16H 10/60* (2018.01); *G16H 70/20* (2018.01);
(Continued)

(58) Field of Classification Search
None
See application file for complete search history.

(56) References Cited

U.S. PATENT DOCUMENTS 5,211,642 A   5/1993   Clendenning
5,475,953 A   12/1995  Greenfield
(Continued)

FOREIGN PATENT DOCUMENTS

CN   104361321 A   2/2015
CN   106056035 A   10/2016
(Continued)

OTHER PUBLICATIONS

Lam, Wai Yin et al., Medication adherence measures: An overview, 2015 Biomed Research International 1-12 (2015) (Year: 2015).*
(Continued)

*Primary Examiner* — Jonathon A. Szumny
*Assistant Examiner* — Nicholas Akogyeram, II
(74) *Attorney, Agent, or Firm* — Carr & Ferrell LLP

(57) ABSTRACT

An application system capable of providing a continuation of care for a user. This is achieved through the assessing of medication compliance, assessing medical testing compliance and providing appropriate care suggestions. The system incorporates medication reminder, medication compliance analytics and the capacity to provide responses to user specific medication inquiries. The system also incorporates medical test assessment capabilities and the capacity to provide basic medical testing protocols. Additionally, as medication and medical testing data are collected, processed and analyzed, they are stored in a zero-click fashion with results being rapidly presented back to the user via an interactive avatar. These data can also be provided in standard of care summaries to users, HIPAA compliant third parties and/or medical care providers.

7 Claims, 12 Drawing Sheets

(51) Int. Cl.
*G16H 10/60* (2018.01)
*G16H 70/20* (2018.01)
*G16H 70/40* (2018.01)
*H04L 67/1097* (2022.01)
*H04L 67/55* (2022.01)

(52) U.S. Cl.
CPC ......... *G16H 70/40* (2018.01); *H04L 67/1097* (2013.01); *H04L 67/55* (2022.05)

(56) References Cited

U.S. PATENT DOCUMENTS

| | | |
|---|---|---|
| 6,665,647 B1 | 12/2003 | Haudenschild |
| 7,233,872 B2 | 6/2007 | Shibasaki et al. |
| 7,445,086 B1 | 11/2008 | Sizemore |
| 7,612,681 B2 | 11/2009 | Azzaro et al. |
| 7,971,141 B1 | 6/2011 | Quinn et al. |
| 8,206,325 B1 | 6/2012 | Najafi et al. |
| 8,771,206 B2 | 7/2014 | Gettelman et al. |
| 9,317,916 B1* | 4/2016 | Hanina ............ A61M 5/31568 |
| 9,591,996 B2 | 3/2017 | Chang et al. |
| 9,972,187 B1 | 5/2018 | Srinivasan et al. |
| 10,387,963 B1 | 8/2019 | Leise et al. |
| 10,628,635 B1 | 4/2020 | Carpenter, II et al. |
| 10,813,572 B2 | 10/2020 | Dohrmann et al. |
| 11,113,943 B2 | 9/2021 | Wright et al. |
| 11,213,224 B2 | 1/2022 | Dohrmann et al. |
| 2002/0062342 A1 | 5/2002 | Sidles |
| 2002/0196944 A1 | 12/2002 | Davis et al. |
| 2004/0109470 A1 | 6/2004 | Derechin et al. |
| 2005/0035862 A1 | 2/2005 | Wildman et al. |
| 2005/0055942 A1 | 3/2005 | Maelzer et al. |
| 2007/0238936 A1 | 10/2007 | Becker |
| 2008/0010293 A1 | 1/2008 | Zpevak et al. |
| 2008/0186189 A1 | 8/2008 | Azzaro et al. |
| 2009/0094285 A1 | 4/2009 | Mackle et al. |
| 2010/0124737 A1 | 5/2010 | Panzer |
| 2011/0126207 A1 | 5/2011 | Wipfel et al. |
| 2011/0145018 A1* | 6/2011 | Fotsch ................ G06Q 50/26 705/3 |
| 2011/0232708 A1 | 9/2011 | Kemp |
| 2011/0275051 A1* | 11/2011 | Hanina ............... G16H 40/67 434/365 |
| 2012/0025989 A1 | 2/2012 | Cuddihy et al. |
| 2012/0075464 A1 | 3/2012 | Derenne et al. |
| 2012/0120184 A1 | 5/2012 | Fornell et al. |
| 2012/0121849 A1 | 5/2012 | Nojima |
| 2012/0154582 A1 | 6/2012 | Johnson et al. |
| 2012/0165618 A1 | 6/2012 | Algoo et al. |
| 2012/0179067 A1 | 7/2012 | Wekell |
| 2012/0179916 A1* | 7/2012 | Staker ............... G06F 9/45558 713/189 |
| 2012/0229634 A1 | 9/2012 | Laett et al. |
| 2012/0253233 A1 | 10/2012 | Greene et al. |
| 2013/0000228 A1 | 1/2013 | Ovaert |
| 2013/0127620 A1 | 5/2013 | Siebers et al. |
| 2013/0145449 A1* | 6/2013 | Busser ................. G06F 21/31 726/7 |
| 2013/0167025 A1 | 6/2013 | Patri et al. |
| 2013/0204545 A1 | 8/2013 | Solinsky |
| 2013/0212501 A1 | 8/2013 | Anderson et al. |
| 2013/0237395 A1 | 9/2013 | Hjelt et al. |
| 2013/0289449 A1 | 10/2013 | Stone et al. |
| 2013/0303860 A1 | 11/2013 | Bender et al. |
| 2014/0055589 A1* | 2/2014 | Bangera ............. A61B 5/4848 348/E7.085 |
| 2014/0128691 A1 | 5/2014 | Olivier |
| 2014/0148733 A1 | 5/2014 | Stone et al. |
| 2014/0171039 A1* | 6/2014 | Bjontegard .......... H04L 67/38 455/414.1 |
| 2014/0171834 A1 | 6/2014 | DeGoede et al. |
| 2014/0232600 A1 | 8/2014 | Larose et al. |
| 2014/0243686 A1 | 8/2014 | Kimmel |
| 2014/0257852 A1 | 9/2014 | Walker et al. |
| 2014/0267582 A1 | 9/2014 | Beutter et al. |
| 2014/0278605 A1 | 9/2014 | Borucki et al. |
| 2014/0330172 A1 | 11/2014 | Jovanov et al. |
| 2014/0337048 A1 | 11/2014 | Brown et al. |
| 2014/0358828 A1 | 12/2014 | Phillipps et al. |
| 2014/0368601 A1* | 12/2014 | deCharms ............ H04L 67/26 348/14.02 |
| 2015/0019250 A1* | 1/2015 | Goodman ............ G16H 40/63 705/2 |
| 2015/0109442 A1 | 4/2015 | Derenne et al. |
| 2015/0169835 A1 | 6/2015 | Hamdan et al. |
| 2015/0359467 A1 | 12/2015 | Tran |
| 2016/0026354 A1 | 1/2016 | Mcintosh et al. |
| 2016/0117470 A1 | 4/2016 | Welsh et al. |
| 2016/0117484 A1* | 4/2016 | Hanina ................. G16H 20/10 705/3 |
| 2016/0154977 A1 | 6/2016 | Jagadish et al. |
| 2016/0217264 A1* | 7/2016 | Sanford ............. H04L 12/1822 |
| 2016/0217270 A1* | 7/2016 | Ferguson ............ G06F 16/245 |
| 2016/0253890 A1 | 9/2016 | Rabinowitz et al. |
| 2016/0267327 A1 | 9/2016 | Franz et al. |
| 2016/0314255 A1 | 10/2016 | Cook et al. |
| 2017/0000387 A1 | 1/2017 | Forth et al. |
| 2017/0000422 A1 | 1/2017 | Moturu et al. |
| 2017/0024531 A1 | 1/2017 | Malaviya |
| 2017/0055917 A1 | 3/2017 | Stone et al. |
| 2017/0140631 A1 | 5/2017 | Pietrocola et al. |
| 2017/0147154 A1 | 5/2017 | Steiner et al. |
| 2017/0192950 A1 | 7/2017 | Gaither et al. |
| 2017/0193163 A1* | 7/2017 | Melle .................... G16H 10/60 |
| 2017/0197115 A1 | 7/2017 | Cook et al. |
| 2017/0213145 A1 | 7/2017 | Pathak et al. |
| 2017/0273601 A1 | 9/2017 | Wang et al. |
| 2017/0337274 A1 | 11/2017 | Ly et al. |
| 2017/0344706 A1 | 11/2017 | Torres et al. |
| 2017/0344832 A1 | 11/2017 | Leung et al. |
| 2018/0001184 A1* | 1/2018 | Tran ................... G09B 19/0038 |
| 2018/0075558 A1* | 3/2018 | Hill, Sr. ................ G06Q 20/10 |
| 2018/0165938 A1 | 6/2018 | Honda et al. |
| 2018/0182472 A1 | 6/2018 | Preston et al. |
| 2018/0189756 A1 | 7/2018 | Purves et al. |
| 2018/0322405 A1 | 11/2018 | Fadell et al. |
| 2018/0360349 A9 | 12/2018 | Dohrmann et al. |
| 2018/0368780 A1 | 12/2018 | Bruno et al. |
| 2019/0029900 A1 | 1/2019 | Walton et al. |
| 2019/0042700 A1* | 2/2019 | Alotaibi ................ G16H 10/20 |
| 2019/0057320 A1 | 2/2019 | Docherty et al. |
| 2019/0090786 A1 | 3/2019 | Kim et al. |
| 2019/0116212 A1 | 4/2019 | Spinella-Mamo |
| 2019/0130110 A1 | 5/2019 | Lee et al. |
| 2019/0164015 A1 | 5/2019 | Jones, Jr. et al. |
| 2019/0196888 A1 | 6/2019 | Anderson et al. |
| 2019/0220727 A1 | 7/2019 | Dohrmann et al. |
| 2019/0259475 A1 | 8/2019 | Dohrmann et al. |
| 2019/0282130 A1 | 9/2019 | Dohrmann et al. |
| 2019/0286942 A1 | 9/2019 | Abhiram et al. |
| 2019/0318165 A1 | 10/2019 | Shah et al. |
| 2019/0385749 A1 | 12/2019 | Dohrmann et al. |
| 2020/0101969 A1 | 4/2020 | Natroshvili et al. |
| 2020/0251220 A1 | 8/2020 | Chasko |
| 2020/0357256 A1 | 11/2020 | Wright et al. |
| 2021/0007631 A1 | 1/2021 | Dohrmann et al. |
| 2021/0273962 A1 | 9/2021 | Dohrmann et al. |
| 2021/0358202 A1 | 11/2021 | Tveito et al. |
| 2021/0398410 A1 | 12/2021 | Wright et al. |

FOREIGN PATENT DOCUMENTS

| | | |
|---|---|---|
| CN | 107411515 A | 12/2017 |
| CN | 111801645 A | 10/2020 |
| CN | 111801939 A | 10/2020 |
| CN | 111867467 A | 10/2020 |
| EP | 3740856 A1 | 11/2020 |
| EP | 3756344 A1 | 12/2020 |
| EP | 3768164 A1 | 1/2021 |
| EP | 3773174 A1 | 2/2021 |
| EP | 3815108 A1 | 5/2021 |
| EP | 3920797 A1 | 12/2021 |
| IN | 202027033318 A | 10/2020 |
| IN | 202027035634 A | 10/2020 |

(56) References Cited

FOREIGN PATENT DOCUMENTS

| | | | |
|---|---|---|---|
| JP | 2002304362 A | 10/2002 | |
| JP | 2005228305 A | 8/2005 | |
| JP | 2016525383 A | 8/2016 | |
| KR | 1020160040078 A | 4/2016 | |
| KR | 1020200105519 A | 9/2020 | |
| KR | 1020200121832 A | 10/2020 | |
| KR | 1020200130713 A | 11/2020 | |
| WO | WO2000005639 A2 | 2/2000 | |
| WO | WO-2011062934 A1 * | 5/2011 | ......... G06F 19/3456 |
| WO | WO2014043757 A1 | 3/2014 | |
| WO | WO2018032089 A1 | 2/2018 | |
| WO | WO2019143397 A1 | 7/2019 | |
| WO | WO2019164585 A1 | 8/2019 | |
| WO | WO2019182792 A1 | 9/2019 | |
| WO | WO2019199549 A1 | 10/2019 | |
| WO | WO2019245713 A1 | 12/2019 | |
| WO | WO2020163180 A1 | 8/2020 | |
| WO | WO2020227303 A1 | 11/2020 | |

OTHER PUBLICATIONS

"International Search Report" and "Written Opinion of the International Searching Authority," Patent Cooperation Treaty Application No. PCT/US2019/034206, dated Aug. 1, 2019, 11 pages.
Rosen et al., "Slipping and Tripping: Fall Injuries in Adults Associated with Rugs and Carpets," Journal of Injury & Violence Research, 5(1), 61-69. (2013).
"International Search Report" and "Written Opinion of the International Searching Authority," Patent Cooperation Treaty Application No. PCT/US2018/057814, dated Jan. 11, 2019, 9 pages.
"International Search Report" and "Written Opinion of the International Searching Authority," Patent Cooperation Treaty Application No. PCT/US2018/068210, dated Apr. 12, 2019, 9 pages.
"International Search Report" and "Written Opinion of the International Searching Authority," Patent Cooperation Treaty Application No. PCT/US2019/021678, dated May 24, 2019, 12 pages.
"International Search Report" and "Written Opinion of the International Searching Authority," Patent Cooperation Treaty Application No. PCT/US2019/025652, dated Jul. 18, 2019, 11 pages.
Bajaj, Prateek, "Reinforcement Learning", GeeksForGeeks.org [online], [retrieved on Mar. 4, 2020], Retrieved from the Internet:<URL:https://www.geeksforgeeks.org/what-is-reinforcement-learning/>, 7 pages.
Kung-Hsiang, Huang (Steeve), "Introduction to Various RL Algorithms. Part I (Q-Learning, SARSA, DQN, DDPG)", Towards Data Science, [online], [retrieved on Mar. 4, 2020], Retrieved from the Internet:<URL:https://towardsdatascience.com/introduction-to-various-reinforcement-learning-algorithms-i-q-learning-sarsa-dqn-ddpg-72a5e0cb6287>, 5 pages.
Bellemare et al., A Distributional Perspective on Reinforcement Learning:, Proceedings of the 34th International Conference on Machine Learning, Sydney, Australia, Jul. 21, 2017, 19 pages.
Friston et al., "Reinforcement Learning or Active Inference?" Jul. 29, 2009, [online], [retrieved on Mar. 4, 2020], Retrieved from the Internet:<URL:https://doi.org/10.1371/journal.pone.0006421 PLoS One 4(7): e6421>, 13 pages.
Zhang et al., "DQ Scheduler: Deep Reinforcement Learning Based Controller Synchronization in Distributed SDN" ICC 2019-2019 IEEE International Conference on Communications (ICC), Shanghai, China, doi: 10.1109/ICC.2019.8761183, pp. 1-7.
"International Search Report" and "Written Opinion of the International Searching Authority," Patent Cooperation Treaty Application No. PCT/US2020/016248, dated May 11, 2020, 7 pages.
"Office Action", Australia Patent Application No. 2019240484, dated Nov. 13, 2020, 4 pages.
"Office Action", Australia Patent Application No. 2018403182, dated Feb. 5, 2021, 5 pages.
"Office Action", Australia Patent Application No. 2018409860, dated Feb. 10, 2021, 4 pages.
Leber, Jessica, "The Avatar will See You Now", MIT Technology Review, Sep. 17, 2013, 4 pages.
"Office Action", India Patent Application No. 202027035634, dated Jun. 30, 2021, 10 pages.
"Extended European Search Report", European Patent Application No. 18901139.8, dated Sep. 9, 2021, 6 pages.
"Office Action", Canada Patent Application No. 3091957, dated Sep. 14, 2021, 4 pages.
"Office Action", Japan Patent Application No. 2020-540382, dated Aug. 24, 2021, 7 pages [13 pages with translation].
"Extended European Search Report", European Patent Application No. 18907032.9, dated Oct. 15, 2021, 12 pages.
Marston et al., "The design of a purpose-built exergame for fall prediction and prevention for older people", European Review of Aging and Physical Activity 12:13, <URL:https://eurapa.biomedcentral.com/track/pdf/10.1186/s11556-015-0157-4.pdf>, Dec. 8, 2015, 12 pages.
Ejupi et al., "Kinect-Based Five-Times-Sit-to-Stand Test for Clinical and In-Home Assessment of Fall Risk in Older People", Gerontology (vol. 62), (May 28, 2015), <URL:https://www.karger.com/Article/PDF/381804>, May 28, 2015, 7 pages.
Festl et al., "iStoppFalls: A Tutorial Concept and prototype Contents", <URL:https://hcisiegen.de/wp-uploads/2014/05/isCtutorial.doku.pdf>, Mar. 30, 2013, 36 pages.
"Notice of Allowance", Australia Patent Application No. 2019240484, dated Oct. 27, 2021, 4 pages.
"Extended European Search Report", European Patent Application No. 19772545.0, dated Nov. 16, 2021, 8 pages.
"Office Action", India Patent Application No. 202027033318, dated Nov. 18, 2021, 6 pages.
"Office Action", Australia Patent Application No. 2018409860, dated Nov. 30, 2021, 4 pages.
"Office Action", Australia Patent Application No. 2018403182, dated Dec. 1, 2021, 3 pages.
"Office Action", Korea Patent Application No. 10-2020-7028606, dated Oct. 29, 2021, 7 pages [14 pages with translation].
"Office Action", Japan Patent Application No. 2020-543924, dated Nov. 24, 2021, 3 pages [6 pages with translation].
"Extended European Search Report", European Patent Application No. EP19785057, dated Dec. 6, 2021, 8 pages.
"Office Action", Australia Patent Application No. 2020218172, dated Dec. 21, 2021, 4 pages.
"Extended European Search Report", European Patent Application No. 21187314.6, dated Dec. 10, 2021, 10 pages.
"Office Action", India Patent Application No. 202027033121, dated Jul. 29, 2021, 7 pages.
"Office Action", Canada Patent Application No. 3088396, dated Aug. 6, 2021, 7 pages.
"Office Action", China Patent Application No. 201880089608.2, dated Aug. 3, 2021, 8 pages.
"Office Action", Japan Patent Application No. 2020-543924, dated Jul. 27, 2021, 3 pages [6 pages with translation].
"Office Action", Australia Patent Application No. 2019240484, dated Aug. 2, 2021, 3 pages.
"Office Action", Canada Patent Application No. 3089312, dated Aug. 19, 2021, 3 pages.

* cited by examiner

MOBILE SYSTEM FOR THE ASSESSMENT OF CONSUMER MEDICATION COMPLIANCE AND PROVISION OF MOBILE CAREGIVING

CROSS REFERENCE TO RELATED APPLICATIONS

The present application claims the priority benefit of U.S. Provisional Patent Application Ser. No. 62/655,582, filed on Apr. 10, 2018 and titled "Mobile System for the Assessment of Consumer Medication Compliance and Provision of Mobile Caregiving," which is hereby incorporated by reference.

FIELD OF INVENTION

The present invention relates to a connected device application system; and, more particularly, to a software application system capable of providing virtual caregiving services by way of a smartphone, tablet or other device having Internet and/or cellular network connectivity, a web browser and voice communication technology.

SUMMARY

It is an object of the present invention to provide access to continued care through interaction with a connected device. As such, in the application functions as a user's virtual caregiver and displays materials related to the user's continuum of care on the display of a user's devices (Smartphone, tablet or computer). Additionally, while having Internet connectivity or cellular network access, connectivity to the Electronic Caregiver Optimum Recognition Blueprint ("ORB") for Emergency Medical Records, cloud-based access to stored user information, Voice over Internet Protocol communication with emergency medical responders, localized voice capture for cloud-based system communications and communication capabilities between user and the Electronic Caregiver Image (ECI) avatar. All capabilities can be displayed on the user's device and provide response capabilities to said user. This will improve provision of continued care to the users of the invention. Additional advantages of the invention are apparent from the detailed embodiment descriptions and accompanying drawings, which set forth embodiments of the invention.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

The detailed embodiments of the current invention are disclosed here. It should be understood, that the disclosed embodiments are merely exemplary of the invention, which may be embodied in multiple forms. Those details disclosed herein are not to be interpreted in any form as limiting, but as the basis for the claims.

In response to the numerous risks associated with aging, and the fact that the population of the United States is rapidly aging, the effort to maintain independence has led to the development of a number of Personal Emergency Response Systems (PERS) or Medical Emergency Response Systems (MERS). Most of these systems have been developed in a manner that include three main components, 1) a radio transmitter in the form of a single button typically worn or the wrist, a belt or around the neck and allow a user to summon help during an emergency, 2) a communicator typically attached to the user's phone line that acts as a speakerphone when the radio transmitter has been activated, and 3) an emergency response center that provides communication to the end user and emergency medical services. While evidence suggests that older adults are experiencing high rates of user satisfaction with home-based PERS, currently available systems do not provide capacity for continuation of care capabilities. Most current PERS/MERS simply provide monitoring for and response to adverse events. Additionally, these current systems do not provide mobile care capabilities tied directly to a smartphone and/or tablet allowing for provision of continued care, immediate and direct contact with emergency responders built into the system, without the need to dial 911, the capability to communicate with a computer simulation, or avatar, acting as a caregiver for the provision of information, and/or services associated with medication, functional movement, and care facilities. Therefore, the present technology has been developed in response to this current lack of capabilities in providing a continuation of care across allied health. Problems requiring health monitoring, assessment and delivery have yet to be fully solved by currently available PERS/MERS. The present technology provides a comprehensive method of electronic caregiving support, health information provision and access to dedicated emergency technicians to directly benefit the user and provide continuation of care. This critical continuation of care information can be displayed on the user's device and/or provided via voice and/or text interaction with the Electronic Caregiver Image (ECI) avatar within the application.

Figure 1:
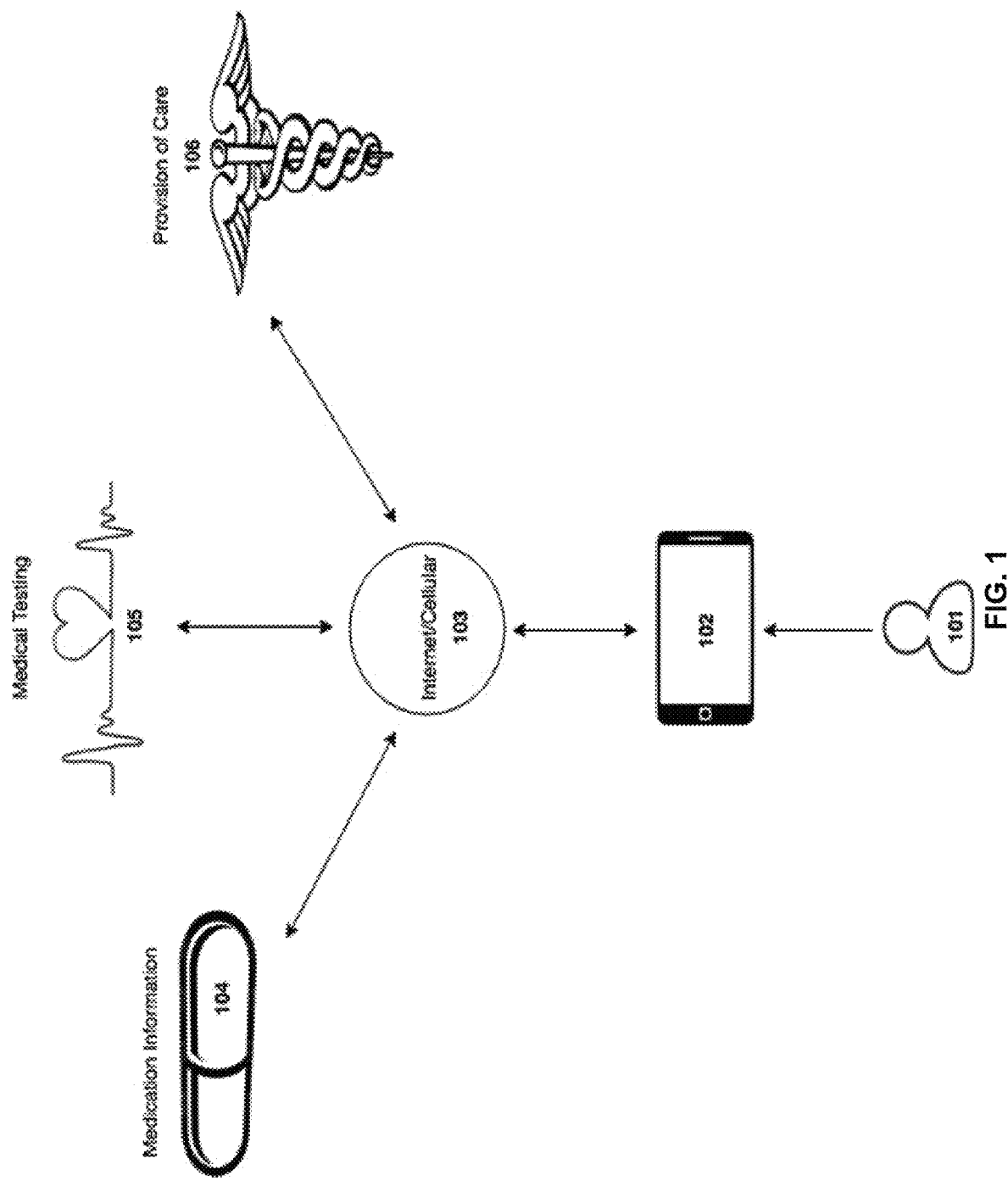
FIG. 1 depicts areas of virtual caregiving provided by the application system interface according to exemplary embodiments of the present technology.

Referring first to FIG. 1, the present application is represented in summary. As such, the user (101) utilizes the application installed on a connected device (102) that connected to either the internet or cellular network (103). The installed application is an Electronic Caregiver developed system capable of providing a continuation of care for user 101. This is achieved through the assessment and/or display of materials and data related to characteristics including the user's current medication characteristics (104), medical testing activities (105) and care provision factors (106). In doing so, this application system provides user 101 with the ability to virtually receive continuation of care and medication monitoring outside of both their typical home setting and the traditional healthcare environment.

Figure 2:
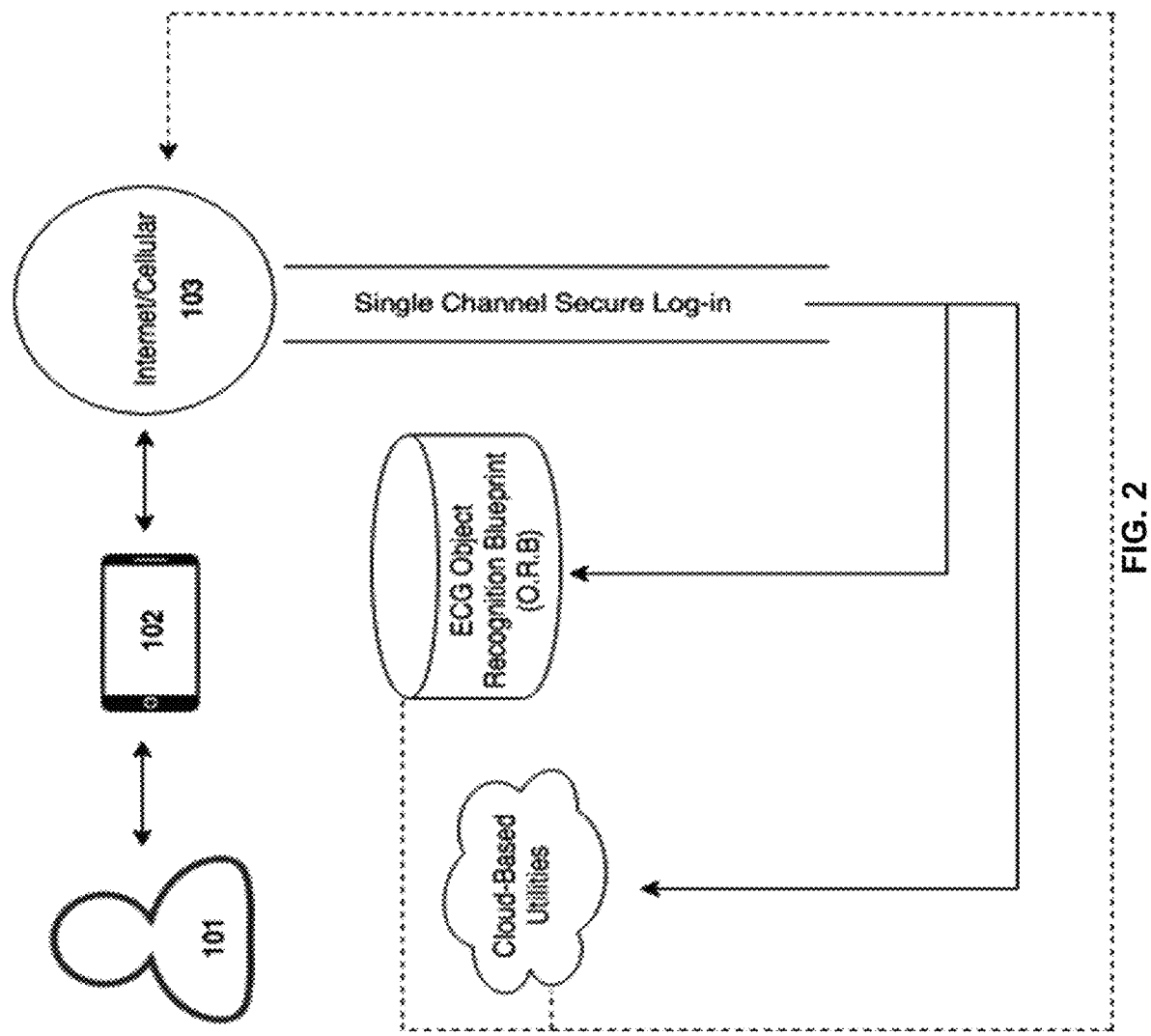
FIG. 2 outlines single pathway login design providing access to various system components according to exemplary embodiments of the present technology.

To provide these continuation of care capabilities, as depicted in FIG. 2, connected device 102 is used to provide user 101 with simultaneous connection to the Electronic Caregiver Object Recognition Blueprint, or ORB (107) and cloud-based utilities (108) via connection to internet or cellular network 103. This connection occurs immediately upon user access of the application and is performed via a single encrypted pathway through Electronic Caregiver derived Application Programming Interface. This single pathway design functions to enhance the security and integrity of the information associated with user 101 such that the application system is capable of providing access to ORB 107 and cloud-based utilities 108 without storing login information associated with user 101. Once simultaneously logged into provided access to ORB 107 and cloud-based utilities 108, user 101 has the capability to utilize the application system to access information and protocols associated with current medication characteristics 104, medical testing activities 105 and care provision factors 106.

Medication Information

To provide accurate information associated with current medication characteristics 104, upon opening the application system on connected device 102, user 101 gains access to a variety of medication data via cloud-based functionality. These data associated with current medication characteristics 104 include: current medication status (109), current medication reminders (110), directions for medication consumption (111), drug side-effects (112), drug-drug interactions (113), drug-food interactions (114), consumption compliance (115) by user 101 and time to refill of medication (116). The information associated with current medication characteristics 104 that is provided via the application system to user 101 is described in Table 1.

To successfully allow the application system to provide information to user 101 describing current medication status 109, the application system provides user 101 with continuous communication capabilities to ORB 107 and cloud-based utilities 108. This connection provides user 101 with access to drop down menu type functionality within the application that contains various medications that can be selected and stored. Once a medication is selected by user 101, further details such as dosage, consumption time and consumption frequency are input and all data associated with the specific medication are transmitted to and stored in cloud-based utilities 108 allowing for information describing current medication status 109 to be consistently provided to and/or accessed by user 101 within the application.

TABLE 1

Application System Provided Information Associated with User Medication.

| Item | Application Provided Information | Application Point of Information Access |
|---|---|---|
| 109 - Medication Status | 1. Medications that have been consumed by user 2. Medications that are to be consumed by user in the future. | Application collected records stored O.R.B and cloud-based data storage services. |
| 110 - Medication Reminders | 1. Time, date and dosage of medication to be consumed. | User input information stored in cloud-based allowing push notifications to be defined. |
| 111 - Consumption Directions | 1. Recommended method for consuming medication. | Programmed functionality for the access of OpenFDA through government provided Application Programming Interface. |
| 112 - Drug Side Effects | 1. Known side-effects associated with each medication. | Programmed functionality for the access of OpenFDA through government provided Application Programming Interface. |
| 113 - Drug-Drug Interactions | 1. Known drug-drug interactions associated with each medication. | Programmed functionality for the access of OpenFDA through government provided Application Programming Interface. |
| 114 - Drug-Food Interactions | 1. Known drug-food interactions associated with each drug. | Programmed functionality for the access of OpenFDA through government provided Application Programming Interface. |

TABLE 1-continued

Application System Provided Information Associated with User Medication.

| Item | Application Provided Information | Application Point of Information Access |
|---|---|---|
| 115 - Medication Compliance | 1. User acknowledgement of appropriate consumption of medication. | Application collected records stored O.R.B and cloud-based data storage services and cloud-based data streaming functionality. |
| 116 - Medication Refill Information | 1. Number of doses remaining in current medication.<br>2. Days remaining until medication is exhausted.<br>3. Number of refills remaining for medication.<br>4. Relevant information for pharmacy where medication was obtained. | Application collected records stored O.R.B and cloud-based data storage services. |

Figure 3:
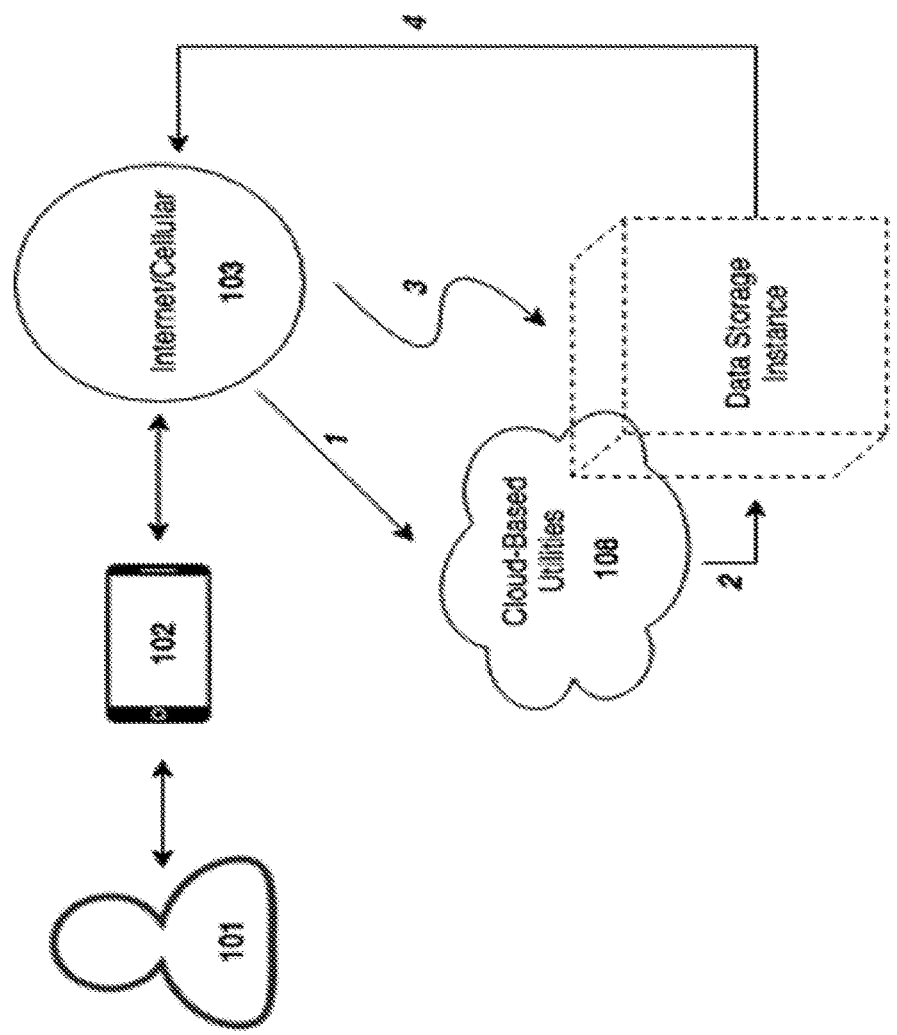
FIG. 3 depicts local device timer creation and push notification transmission within the application system according to exemplary embodiments of the present technology.

The application system embodies the capability for a user to enter local device timers for the provision of current medication reminders 110 to user 101 through the use of local device timers. FIG. 3 demonstrates how these local device timers are transmitted and stored in cloud-based database(s) following their entry by the user. This information storage allows user 101 to create push notifications that are transmitted from cloud-based utilities to the application at the indicated time of medication consumption that inform user 101 of the appropriate medication, the dosage and consumption instructions to be consumed.

The following table explains embodiments of the present technology as depicted in FIG. 3:

| 1 | 101 is logged into 108 following access of the application system. |
| 2 | Following authentication, 101 gains access to cloud-based data storage instances. |
| 3 | 101 inputs medication reminder data through 102 such that data are transmitted and stored in cloud-based data storage instance and local device timer is established. |
| 4 | Device timer information stored in 108 is retrieved and a push notification is transmitted to 101 through 102 at designated time. |

Figure 4:
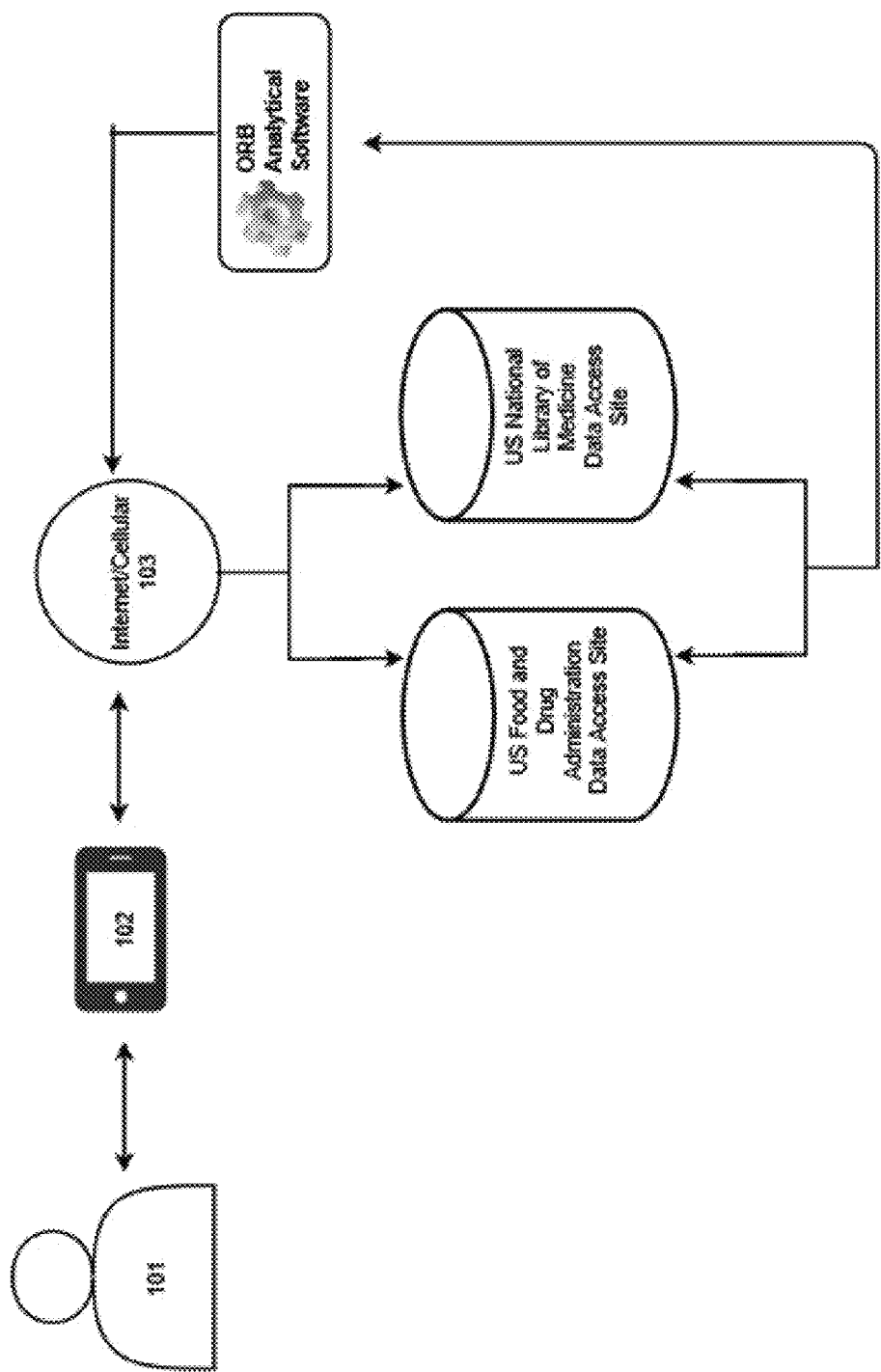
FIG. 4 outlines the data flow pathway for medication data according to exemplary embodiments of the present technology.

In order for the application system to provide information to user 101 that describe directions for medication consumption 111, drug side-effects 112, drug-drug interactions 113, and drug-food interactions 114, the current application system utilizes mechanisms that include; the generation of a user profile upon login to ORB through the mobile device interface. Following the login, user 101 immediately has the capability to query for customizable drug interaction data maintained with the ORB environment. These data, housed within the ORB environment, will be collected using available an OpenFDA API capable of scrubbing both the United States National Library of Medicine Data Access site and the United States Food and Drug Administration Data access site (containing government provided, open-source, documents/databases that contain information describing drug adverse events, drug product labeling, and drug recall enforcement reports). Upon retrieval of these drug data, exportation of the data occurs through the Electronic Caregiver interface such that analysis and storage occurs within ORB environment. As depicted in FIG. 4, this process provides user 101 with on-demand access to a variety of medication information that may include; 1) side effects, 2) personal usage history, 3) food and drug interactions, 4) adverse event reports, and 5) available dosages. This query data can be stored to a user profile that can be presented to a physician at any time. Additionally, the company derived analytic processes housed within ORB provide consistent assessment of user 101 medication data. As such, when two medications scheduled for consumption by user 101 pose a risk of possible interaction, the experiencing of known side effects or other adverse reaction, an alert will be put through to the user interface for review by user 101.

For the tracking of, and provision of information describing consumption compliance 115, the application system utilizes multiple methods that include manual data input by user 101 and video analytics made possible via the manufacturer developed camera system installed into connected device 102. With regard to the capability of allowing user 101 to acknowledge compliance with their medication regiment through manual data input, utilization of the touch screen capabilities of connected device 102 are incorporated. As such user 101 is provided with the previously described push notification for current medication reminders 110 and prompted with pop-up "Yes" and "Not Now" buttons depicted in FIG. 5. When user 101 selects the "Yes" button they progress to the medication page in the user interface displayed on connected device 102. Following consumption of the medication, user 101 inputs an acknowledgement of medication consumption into the application through continued use of the touch screen capabilities of connected device 102. Upon manual acknowledgement of consumption compliance 115 by user 101, an update of cloud-based medication data associated with user 101 is processed and a cessation of current medication reminders 110 occurs.

Figure 5:
FIG. 5 provides a representation of the selection provided to users during medication reminder according to exemplary embodiments of the present technology.
Figure 6:
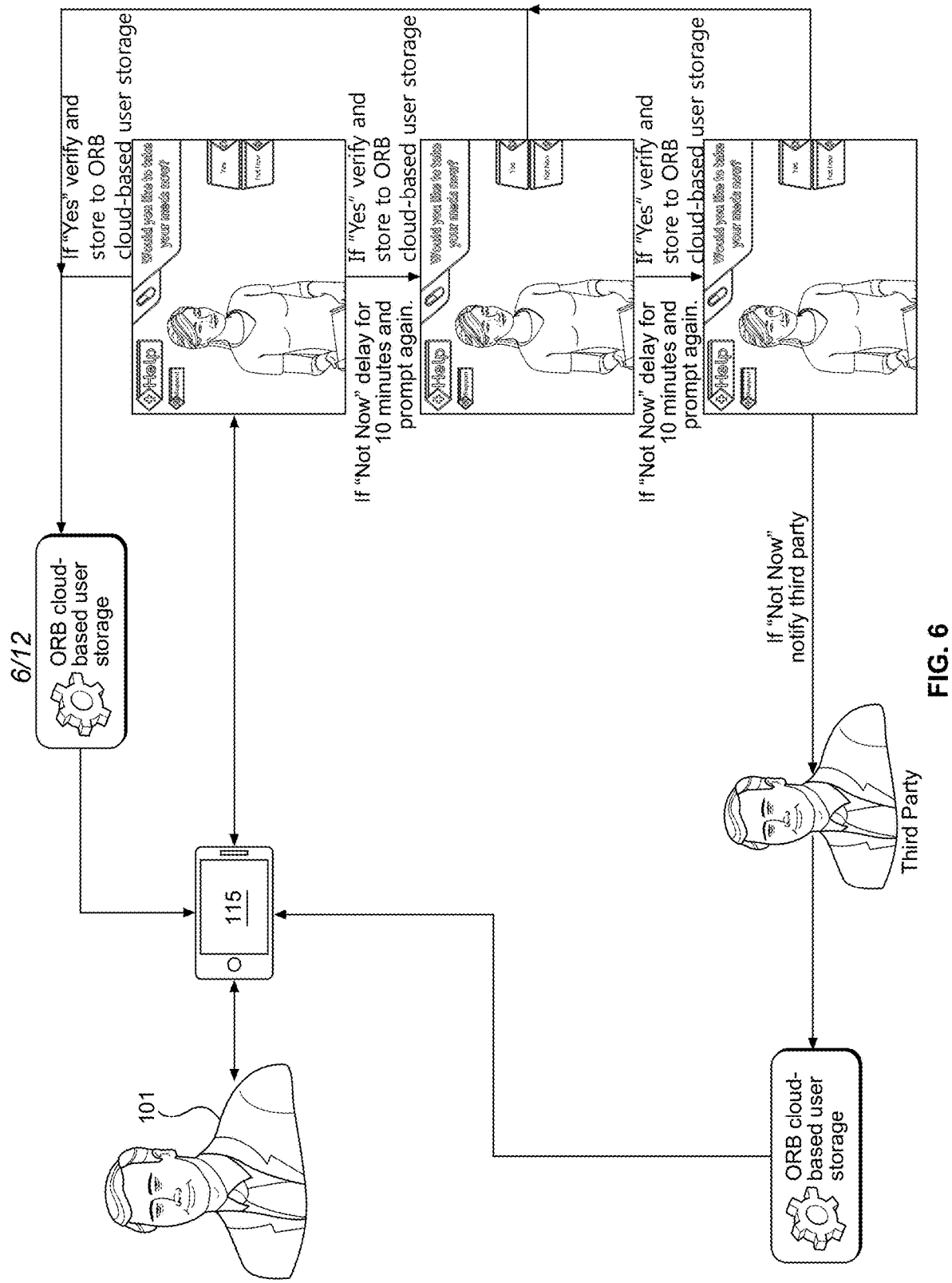
FIG. 6 demonstrates what occurs throughout a medication consumption delay process according to exemplary embodiments of the present technology.

Continuing with manual input of consumption compliance 115, the application system provides user 101 with the option to delay medication consumption using the "Not Now" option also depicted in FIG. 5. The application allows this delay of consumption compliance 115 to occur for up to a maximum of 30 minutes. When user 101 selects the option to delay consumption following the receipt of current medication reminders 110, the application system initiates a 10-minute delay period. At the conclusion of the 10-minute delay, user 101 again receives current medication reminders 110 and is prompted with "Yes" and "Wait" options. The available "Wait" option may be activated up to two times without additional input from user 101. When the activation of the delay occurs a third time, the application system immediately notifies user 101 that their indicated responsible party will be contacted if consumption of medication is not acknowledged. In instances where user 101 does not acknowledge medication consumption following the final reminder, the notification of responsible party protocol displayed in FIG. 6 is activated.

Figure 7:
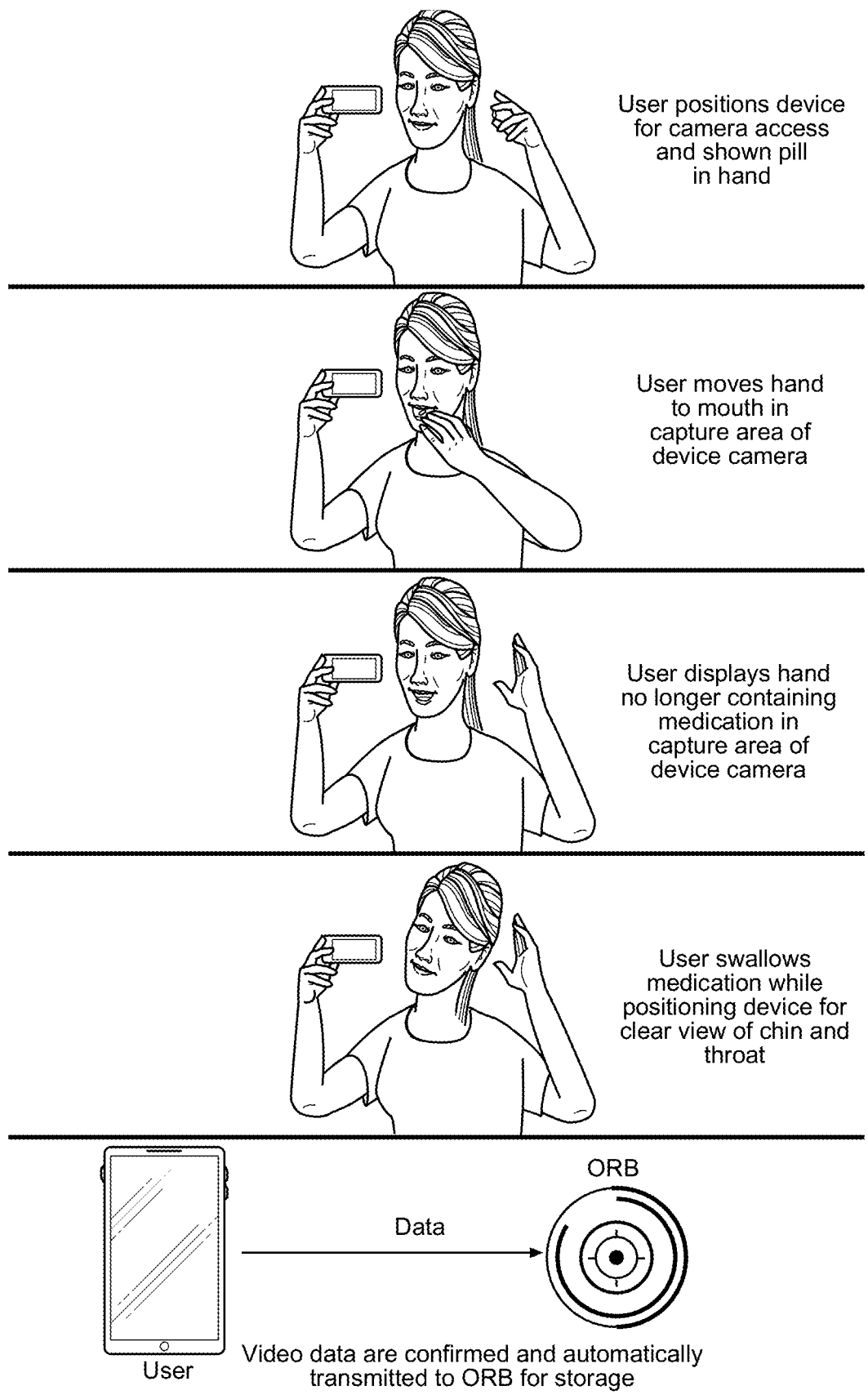
FIG. 7 is a representation of a video analytic process for medication consumption verification according to exemplary embodiments of the present technology.

FIG. 7 demonstrates the utilization of mobile device camera system in connected device 102 to perform medication consumption verification by way of video analytics. User 101 will place self in front of connected device 102 where system included facial recognition software and object recognition software will verify user 101 and medication being taken. Included motion tracking software will then be used to monitor the actions of user 101 during medication consumption such that confirmation of the following actions occur; 1) medication is placed within the hand of user 101, 2) user 101 reorients the hand in front of their mouth, 3) the medication to be consumed is transferred from the hand to the mouth, 4) user 101 reorients the hand away from the mouth and the hand no longer contains the medication to be consumed and 5) user 101 completes a swallowing action. These verified outputs of these actions will be transmitted to and stored via the ORB environment for appropriate utilization.

Also associated with consumption compliance 115, the application system provides user 101 with the capability to review any medication reminders that would be considered "missed". In instances where user 101 does not adhere to the medication protocol and their indicated third party is contacted, the application system provides user 101 or their indicated third part with the ability to review the medications that were not taken correctly. This allows the tracking and storage of medication adherence in cloud-based utilities and provides user 101 with the opportunity to safely consume any medications that were missed. Throughout the utilization of medication tracking aspect, the connection to the cloud-based utilities and the capability of the application system to provide directions for medication consumption 111, drug side-effects 112, drug-drug interactions 113 and drug-food interactions 114 potential problems associated with medication(s) being consumed at the wrong time or too closely to another medication can be identified and monitored.

The application system also embodies the capability for allowing for medication refill information (116) to be provided consistently to user 101. With regard to time to refill of medication 116, user 101 makes use of the system connection to both ORB 107 and cloud-based utilities 108 provided by the application system to input information regarding refill conditions for all current medications consumed by user 101. Upon selection of medication form the drop down menu functionality provided via connected device 102, user 101 inputs data describing the number of doses associated with the medication and the number of available refills. Following the input of these data by user 101, the application system utilizes cloud-based compute functionality resulting in the transmission of these medication data to cloud-based storage databases. Similar to current medication reminders 110, during this process local device timers for medication refill are created by user 101, transmitted and stored in cloud-based database(s) following their entry by the user. This information storage allows the creation of push notifications informing user 101 of pending medication refill needs that are transmitted from cloud-based utilities to the application at indicated times. These refill indicators are transmitted to user 101 at intervals of 3 days, 2 days and 1 day to user 101 exhausting their current medication. At the time of each refill reminder, user 101 is provided with the option to confirm the execution of any refill orders in a similar fashion to that described for consumption compliance 115. Upon the transmission of the 1-day reminder from the application system to user 101, user 101 is notified that a failure to execute a refill order will result in the activation of the indicated responsible party. Failing to indicate the execution of a refill order following the 1-day reminder, the application system immediately notifies user 101 that their indicated responsible party will be contacted if refill order execution is not acknowledged. In instances where user 101 does not acknowledge refill of medication following the 1-day reminder, the notification of responsible party protocol is activated and carried out.

Medical Testing

The application system embodies the capacity to enhance compliance with medical testing protocols. Similar to current medication reminders 110, user 101 inputs medical testing data into connected device 102 and those data are transmitted and stored in ORB 107 and cloud-based utilities 108. Following storage of medical testing data, a local device timer is created, transmitted and stored in cloud-based data storage instances. This information storage allows user 101 to create push notifications that are transmitted from cloud-based utilities to the application at the indicated time of medical testing and informs user 101 of the pending test to be completed, the procedures by which the test is to be completed and any additional information relevant to the specific medical test.

A subsequent embodiment of the application system is the ability to store and analyze data associated with medical testing protocols input by user 101. Following the creation of a customizable user profile within ORB 107 medical testing data can be stored and accessed by user 101 or responsible parties under HIIPA compliance. Additionally, various internal analyses techniques can be applied to the stored test data so that analytic outputs can be provided to user 101 or responsible parties. These analytic outputs can be utilized by user 101, a responsible party or a physician for additional review. The user can also input day to day symptoms on how they felt prior to and during the various medical tests that can provide insight into various aspects of the medical testing associated with user 101.

Provision of Care

Figure 8:
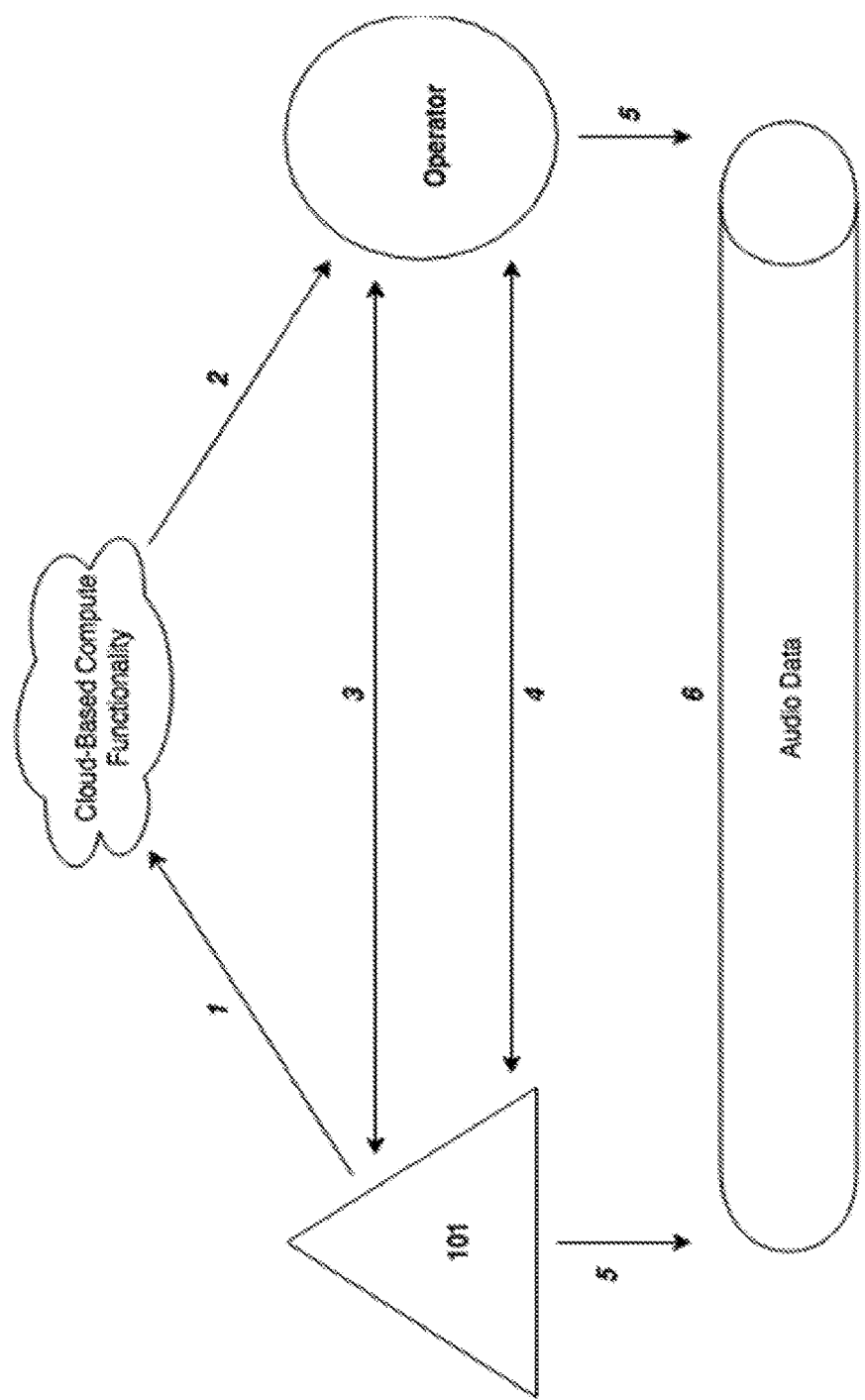
FIG. 8 outlines Voice over internet Protocol actions according to exemplary embodiments of the present technology.

The current application embodies the provision of access to an emergency call center staffed with dedicated emergency responders to user 101. As depicted in FIG. 8, the application system includes company developed Voice over Internet Protocol (VoIP) capabilities to provide user 101 with direct voice access to emergency responders by way of cloud-based real-time streaming utilities. This is achieved through an emergency response action initiated by user 101 through use of connected device 102. The initiation of this emergency response action by user 101 is followed by an immediate connection sequence to a queued emergency operator. Following the connection, both user 101 and the emergency operator enter a sessionized instance of data exchange during which audio data exchange between user 101 and operator are encrypted. In the application system, this sessionized audio data exchange is achieved using one communication channel in which data tags are assigned to each record of transmitted data.

The following table explains embodiments of the present technology as depicted in FIG. 8:

| | |
|---|---|
| 1 | User places call via mobile device touch screen capabilities. |
| 2 | Cloud-based compute capacity processed user call and assigns queued operator to call. |
| 3 | Session information is exchanged between user device and operator. |
| 4 | Session identification and anonymized identification is sent to user and operator so that streaming session begins. |
| 5 | User and operator are connected to encrypted data stream. |
| 6 | Single channel encrypted data stream is utilized to allow communication between user and operator. |

Figure 9:
FIG. 9 is a depiction of an Electronic Caregiver Image (ECI) avatar according to exemplary embodiments of the present technology.
Figure 10:
FIG. 10 is a full body representation of the ECI avatar according to exemplary embodiments of the present technology.

The application system embodies the ability to incorporate existing local voice capture technology to allow the user to communicate directly with the Electronic Caregiving Image (ECI) avatar by voice. This local voice capture communication capability with the ECI avatar allows the user to make voice based inquiries of their medical data. Responses to these queries are provided via the ECI avatar depicted in FIG. 9 and FIG. 10. In such, user 101 can use standard voice communication hardware to vocally communicate with the ECI avatar regarding current medication status 109, current medication reminders 110, directions for medication consumption 111, drug side-effects 112, drug-drug interactions 113, drug-food interactions 114, consumption compliance 115 and time to refill of medication 116. This aspect of the application system also provides redundancy in that when confusion regarding current care status and/or needs occur, user 101 is capable of communicating with ECI avatar to request clarifying information based on available care data.

The application system also provides user 101 with the capacity to identify care provision facilities though the application system interface. As such, user 101 is provided with the capacity to utilize GPS through a connected mobile device that interacts with the ECI avatar. This capacity provides user 101 with available map data of every emergency/urgent care facility available in the vicinity of the current location of user 101. This embodiment is particularly useful when user 101 is in an unfamiliar area and comes experiences an adverse event that may require medical intervention. By accessing the ECI avatar though hand held or voice interaction, user 101 can request information regarding care facilities. Following this request for information, the application system utilizes the GPS capabilities of the connected device and provides the location and directions to the nearest care facility. This can be achieved within the system using ECI avatar communication direct with user 101, user 101 can be refer to a list of directions displayed on connected device 102 or user 101 can be provided map data detailing the fastest route to the nearest facility.

Application System Use Examples

Drug Interaction Query.

As user 101 prepares to consume a prescribed medication, they can make a simply inquiry of the ECI avatar by asking "Addison, I am preparing to take medication X after lunch. Are there any known food-drug interactions associated with medication X?" Upon this query, the application system will access ORB to identify any interaction data that has been previously retrieved from the FDA and/or NLM data sources. Upon accessing these data and identifying a potential drug-food interaction (e.g.—alcohol), the ECI avatar will respond to user 101 with a statement such as, "Mrs. Caroline, the medication you indicated has been shown to interact with alcohol. I would recommend that you not consume any alcoholic beverages during your lunch."

Medical Testing Result Analysis.

Following the completion of daily blood pressure testing on the final day of the month, user 101 can be provided a breakdown of the trends associated with their data. As such, if the results of the trend analysis indicated a slow and steady increase in blood pressure measurements over the course of the month, the application system can suggest user 101 consider making an appointment with the appropriate health care provider. If the results of the trend analysis indicate consistency for the month of blood pressure testing results, the application system can provide positive feedback to user 101 indicating their hard work appears to be resulting in successful regulation of their blood pressure.

Figure 11:
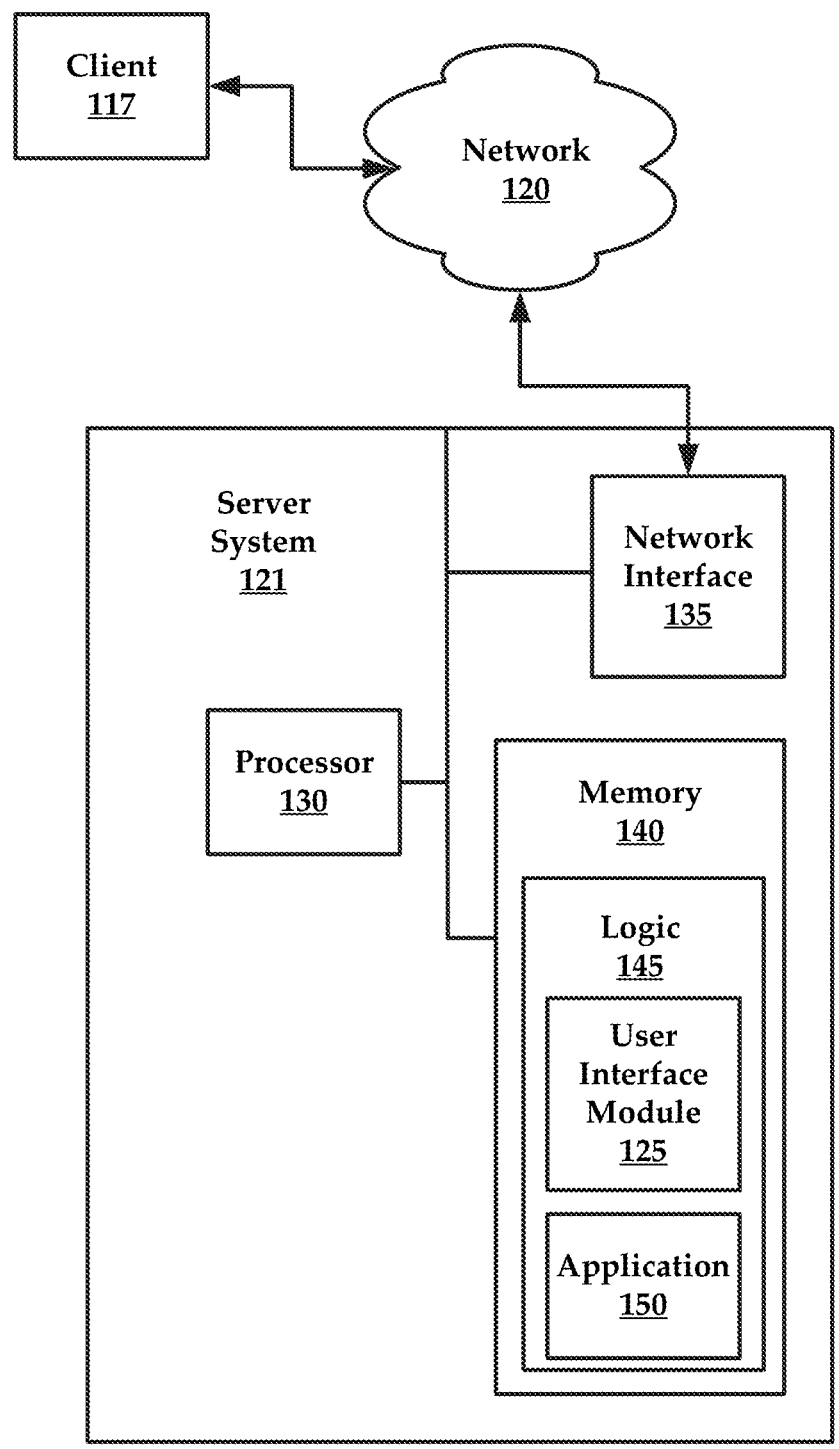
FIG. 11 is a schematic diagram of an exemplary computing architecture that can be used to practice aspects of the present technology.

FIG. 11 illustrates an exemplary architecture for practicing aspects of the present technology. The architecture comprises a server system, hereinafter "system 121" that is configured to provide various functionalities, which are described in greater detail throughout this document. Generally the system 121 is configured to communicate with client devices, such as client 117. The client 117 may include, for example, a computing system (e.g., connected device 102) or other similar computing device. An example of a computing device that can be utilized in accordance with the present technology is described in greater detail with respect to FIG. 12.

The system 121 may communicatively couple with the client 117 via a public or private network, such as network 120 (e.g., internet or cellular network 103). Suitable networks may include or interface with any one or more of, for instance, a local intranet, a PAN (Personal Area Network), a LAN (Local Area Network), a WAN (Wide Area Network), a MAN (Metropolitan Area Network), a virtual private network (VPN), a storage area network (SAN), a frame relay connection, an Advanced Intelligent Network (AIN) connection, a synchronous optical network (SONET) connection, a digital T1, T3, E1 or E3 line, Digital Data Service (DDS) connection, DSL (Digital Subscriber Line) connection, an Ethernet connection, an ISDN (Integrated Services Digital Network) line, a dial-up port such as a V.90, V.34 or V.34bis analog modem connection, a cable modem, an ATM (Asynchronous Transfer Mode) connection, or an FDDI (Fiber Distributed Data Interface) or CDDI (Copper Distributed Data Interface) connection. Furthermore, communications may also include links to any of a variety of wireless networks, including WAP (Wireless Application Protocol), GPRS (General Packet Radio Service), GSM (Global System for Mobile Communication), CDMA (Code Division Multiple Access) or TDMA (Time Division Multiple Access), cellular phone networks, GPS (Global Positioning System), CDPD (cellular digital packet data), RIM (Research in Motion, Limited) duplex paging network, Bluetooth radio, or an IEEE 802.11-based radio frequency network. The network 120 can further include or interface with any one or more of an RS-232 serial connection, an IEEE-1394 (Firewire) connection, a Fiber Channel connection, an IrDA (infrared) port, a SCSI (Small Computer Systems Interface) connection, a USB (Universal Serial Bus) connection or other wired or wireless, digital or analog interface or connection, mesh or Digi® networking.

The system 121 generally comprises a processor, 130, a network interface 135, and a memory 140. According to some embodiments, the memory 140 comprises logic (e.g., instructions) 145 that can be executed by the processor 130 to perform various methods. For example, the logic may include a user interface module 125 as well as a data aggregation and correlation application (hereinafter application 150) that is configured to provide the functionalities described in greater detail herein including tracking and evaluating neurological disease. In some instances, application 150 is the application system providing virtual caregiving services described herein. In various instances, the user interface module 125 enables the customizable interface 200 or the user interfaces shown in FIG. 5 and FIG. 6 and the avatars shown in FIG. 9 and FIG. 10.

It will be understood that the functionalities described herein, which are attributed to the system 121 and application 150 may also be executed within the client 117. That is, the client 117 may be programmed to execute the functionalities described herein. In other instances, the system 121 and client 117 may cooperate to provide the functionalities described herein, such that the client 117 is provided with a client-side application that interacts with the system 121 such that the system 121 and client 117 operate in a client/server relationship. Complex computational features may be executed by the system 121, while simple operations that require fewer computational resources may be executed by the client 117, such as data gathering and data display.

In general, the user interface module 125 may be executed by the system 121 to provide various graphical user interfaces (GUIs) that allow users to interact with the system 121. For example, the user interfaces shown in FIG. 5 and FIG. 6 and the avatars shown in FIG. 9 and FIG. 10. In some instances, GUIs are generated by execution of the application 150 itself. Users may interact with the system 121 using, for example, a client 117. The system 121 may generate web-based interfaces for the client 117.

Figure 12:
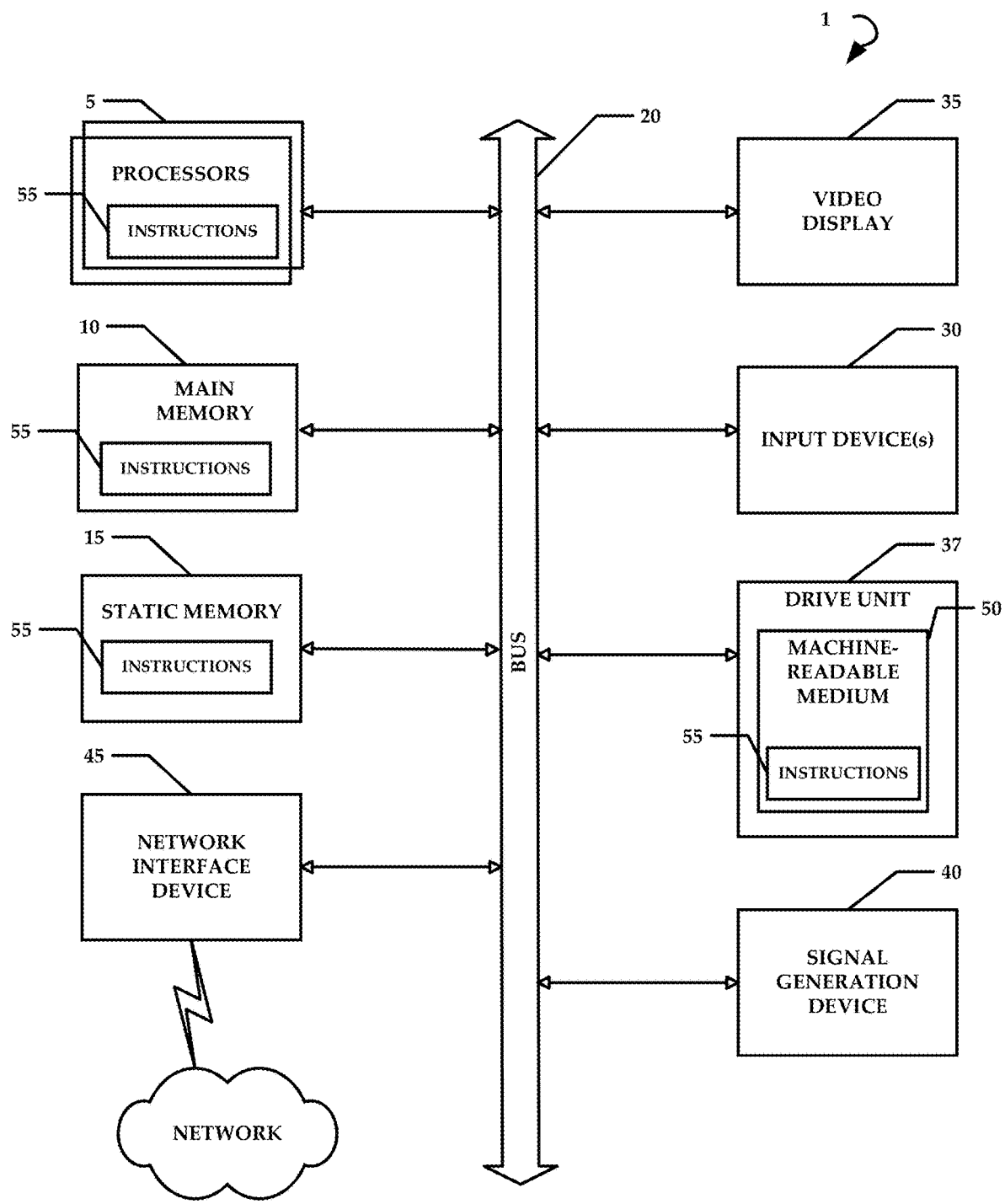
FIG. 12 illustrates a computer system according to exemplary embodiments of the present technology.

FIG. 12 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network (e.g., network 120, see FIG. 11) via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In the description, for purposes of explanation and not limitation, specific details are set forth, such as particular embodiments, procedures, techniques, etc. in order to provide a thorough understanding of the present technology. However, it will be apparent to one skilled in the art that the present technology may be practiced in other embodiments that depart from these specific details.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, it should be understood that they have been presented by way of example only, and not limitation. The descriptions are not intended to limit the scope of the present technology to the particular forms set forth herein. To the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

What is claimed is:

1. A system capable of running on an internet and/or cellular network, the system comprising:
   a connected device having an Electronic Caregiver application installed thereon, the connected device being capable of providing virtual continued care using an Electronic Caregiving Image (ECI) avatar within the Electronic Caregiver application;
   an Object Recognition Blueprint (ORB) implemented on a first computing device, the ORB storing medication data comprising customizable drug interaction data for a user; and
   a variety of cloud-based storage utilities implemented on one or more second computing devices, the cloud-based storage utilities storing current medication reminders for the user, the current medication reminders including a time, date and dosage of medication to be consumed, and the connected device is connectable to the ORB and the variety of cloud-based storage utilities via the internet and/or cellular network;
   wherein immediately upon user access of the Electronic Caregiver application, a single encrypted pathway system is utilized to connect the connected device to the Object Recognition Blueprint (ORB) and the variety of cloud-based storage utilities wherein at a time of medication consumption indicated in a current medication reminder data the cloud-based storage utilities transmit push notifications to the Electronic Caregiver application in the connected device to inform the user of appropriate medication and dosage of medication to be consumed;
   wherein the connected device comprises a mobile device camera system having facial recognition software for recognizing the user when in front of the mobile device camera system, object recognition software for recognizing medication being taken, and motion recognition software for monitoring the actions of the user during the medication consumption, wherein the motion recognition software is configured to monitor user actions of: medication is placed within a hand of the user; the user reorients the hand in front of their mouth; the medication to be consumed is transferred from the hand to the mouth;
   the user reorients the hand away from the mouth and the hand no longer contains the medication to be consumed; and
   the user completes a swallowing action with the mobile device camera system of the connected device being in a position for view of chin and throat of the user while recording an audible gulp of the user, wherein the connected device is configured to transmit a verification output verifying that the user actions have been performed to the ORB.

2. The system of claim 1, further comprising provision of continuous and secure access to cloud-based storage of user information.

3. The system of claim 2, wherein the cloud-based storage of user information is consistently and automatically updated.

4. The system of claim 1, wherein an environment of the Object Recognition Blueprint (ORB) comprises an OpenFDA API, the OpenFDA API allowing scrubbing of government provided, open-source, documents and databases, the government provided, open-source, documents and databases comprising information describing drug adverse events and drug recall enforcement reports.

5. The system of claim 1, wherein an environment of the Object Recognition Blueprint (ORB) comprises derived analytic processes of assessment of user medication data, the derived analytic processes of assessment of user medication comprising drug interaction risk data, the drug interaction risk data comprising data describing at least one of: when two medications scheduled for consumption by a user pose a risk of possible interaction by the two medications, known side effects to the user of the two medications, or an adverse reaction of the user of the two medications.

6. The system of claim 1, wherein the variety of cloud-based storage utilities comprise a direct voice access, Voice over Internet Protocol (VoIP), real-time streaming utility, the direct voice access, Voice over Internet Protocol (VoIP), real-time streaming utility providing direct voice access to an emergency responder for the user by an initiation of an emergency response action sequence, the initiation of the emergency response action sequence comprising an immediate connection sequence to a queued emergency operator using a sessionized instance of audio data exchange between the emergency responder and the user allowing encryption of the audio data, the sessionized instance of audio data exchange using one communication channel with data tags assigned to each record of transmitted data of the audio data exchange.

7. The system of claim 6, wherein the direct voice access, Voice over Internet Protocol (VoIP), real-time streaming utility allows the user to communicate directly with the Electronic Caregiving Image (ECI) avatar using local voice capture communication with the Electronic Caregiving Image (ECI) avatar, the local voice capture communication with the Electronic Caregiving Image (ECI) avatar comprising voice based inquiries by a user of medical data of the user using the Electronic Caregiving Image (ECI) avatar.

* * * * *